United States Patent [19]

Demus et al.

[11] Patent Number: 4,601,846

[45] Date of Patent: Jul. 22, 1986

[54] LIQUID CRYSTAL SUBSTANCES FOR THE GUEST-HOST EFFECT

[75] Inventors: Dietrich Demus; Horst Zaschke, both of Halle; Gerhard Pelzl, Halle-Neustadt; Hartmut Enzenberg, Halle; Andreas Isenberg, Eisleben, all of German Democratic Rep.

[73] Assignee: VEB Werk fuer Fernsehelektronik im VED Kombinat Mikroelektronik, Berlin, Fed. Rep. of Germany

[21] Appl. No.: 599,864

[22] Filed: Apr. 13, 1984

[30] Foreign Application Priority Data

Apr. 29, 1983 [DD] German Democratic Rep. ... 250330

[51] Int. Cl.$^4$ ............. C09K 3/34; G02F 1/13; C07D 257/08; C07D 257/12
[52] U.S. Cl. ............. 252/299.1; 252/299.5; 252/299.61; 350/349; 350/350 R; 350/350 S; 534/577; 544/179; 544/359
[58] Field of Search ............. 252/299.1, 299.61, 299.5; 544/179, 359; 350/350 R, 350 S, 349; 534/577

[56] References Cited

U.S. PATENT DOCUMENTS

| | | | |
|---|---|---|---|
| 4,311,610 | 1/1982 | Zaschke et al. | 252/299.61 |
| 4,356,103 | 10/1982 | Schubert et al. | 252/299.61 |
| 4,358,393 | 11/1982 | Zaschke et al. | 252/299.61 |
| 4,358,589 | 11/1982 | Schubert et al. | 252/299.61 |
| 4,438,268 | 3/1984 | Zaschke et al. | 252/299.62 |
| 4,490,305 | 12/1984 | Eidenschink et al. | 252/299.5 |

FOREIGN PATENT DOCUMENTS

| | | | |
|---|---|---|---|
| 36771 | 9/1981 | European Pat. Off. | 252/299.61 |
| 3227916 | 3/1984 | Fed. Rep. of Germany | 252/299.61 |
| 151950 | 11/1981 | German Democratic Rep. | 252/299.61 |
| 56-18675 | 2/1981 | Japan | 252/299.1 |
| 56-32579 | 4/1981 | Japan | 252/299.1 |
| 56-62874 | 5/1981 | Japan | 252/299.1 |
| 56-90072 | 7/1981 | Japan | 252/299.61 |
| 56-83481 | 7/1981 | Japan | 252/299.61 |
| 56-116775 | 9/1981 | Japan | 252/299.61 |
| 57-14584 | 1/1982 | Japan | 252/299.61 |
| 58-88371 | 5/1983 | Japan | 252/299.61 |

OTHER PUBLICATIONS

Werbel, L. M., et al., J. Heterocyclic Chem., vol. 16, pp. 881–894 (Jul. 1979).
Demus, D., et al., Mol. Cryst. Liq. Cryst., vol. 56 (Letters), pp. 115–121 (1979).
Zaschke, H., et al., "Synthesis and Properties of Liquid Crystalline Heterocycloalkanes", Liq. Cryst. & Ordered Fluids, vol. 4, pp. 75–87, Plenum Press, N.Y., 1984, Reporting Proceedings of ACS Mar. 29–Apr. 1, 1982 in Las Vegas, Nevada.
Karamysheva, L. A., et al., Advances in Liquid Crystal Research and Applications, Ed. Bata, L., Pergamon Press, Oxford, pp. 997–1002 (1980).

*Primary Examiner*—Teddy S. Gron
*Attorney, Agent, or Firm*—Jordan and Hamburg

[57] ABSTRACT

The invention relates to liquid crystal compounds for the guest-host effect having a positive contrast, pure red color and exhibiting excellent stability. The compounds herein are derivatives of tetrazine of the general formula:

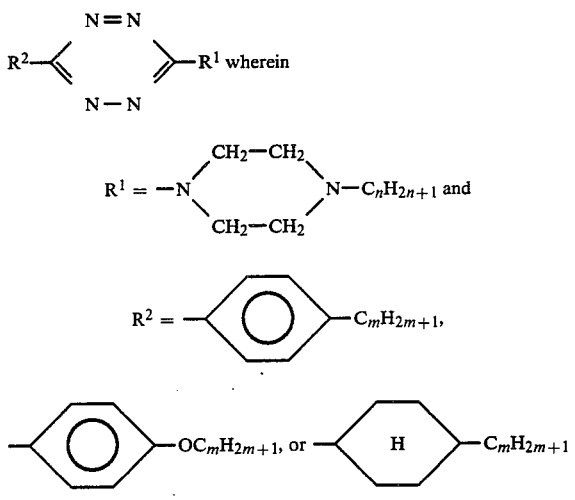

in which m and n are 1 to 10.

Other related compounds, mixtures and compositions thereof, and opto-electronic displays are described also.

21 Claims, No Drawings

LIQUID CRYSTAL SUBSTANCES FOR THE GUEST-HOST EFFECT

BACKGROUND OF THE INVENTION

The invention relates to opto-electronic components, and, more particularly, to liquid crystal nematic substances for the chromatic display of numbers, symbols and images.

It has been known for some time that chromatic liquid-crystalline mixtures can be used for the production of opto-electronic components and displays, based on the guest-host effect G. H. Heilmeier, L. A. Zanoni; Appl. Phys. Letters 13, 91 (1968). Mixtures which use the guest-host effect consist of nematic matrix substances, and one or more dyestuffs, which are oriented because of the anisotropy of the matrix. If the dyestuff has an anisotropy of the light absorption (dichroism), it is possible to simultaneously change the absorption characteristics due to the reorientation of the matrix in an electrical field. In general, such dyestuffs have a polarization level of which oscillates parallel to the longitudinal axis of the obling dyestuff molecule.

In nematic matrix substances with a positive dielectric anisotropy, this means that in the absence of an electrical field these substances are chromatic, while when contacting the field they become colorless. In displays this results in the observation of colorless numbers and symbols on a colored background, i.e., a so called "display with a negative contract," which in general is disadvantageous. A "display with a positive contrast" could be achieved by using nematic matrix substances having a negative dielectric anistropy. Suitable nematic matrix substances for this purpose, however, are not available.

A "display with positive contrast" may be made by using dyestuffs having a negative dichroism, as well, which are dissolved in nematic matrix substances with positive dielectric anisotrophy. Such dyestuffs also must exhibit good stability, particularly against light, and, as well, against thermal, chemical and electrical influences. They must be sufficiently soluble in nematic substances to provide a good chromatic contrast. It is already known that derivatives of tetrazine, which themselves have liquid crystalline characteristics, are dyestuffs with negative dichroism (see DD-Patents Nos. 137 117, 137,118, 137,242, 151,950; Fukui et al., 8, Internat. Liquid crystal Conf. Kyoto 1980, Abstract No. E-15 p). However previously known tetrazine derivatives exhibit an absorption maximum of 550 nm, only, i.e., a reddish-purple color, and this hue cannot be changed.

Accordingly, it is the object of the invention to provide liquid crystal substances for the guest-host effect with positive contrast with a pure red color, and which are particularly stable against light, and also against thermal, chemical and electrical effects.

Another object of the invention to provide chromatic liquid crystalline compounds which allow the preparation of mixtures and compositions for the guest-host effect having a positive contrast and pure red color.

Still another object herein is to provide a positive contrast opto-electronic display component comprising a dye having a negative dichroism and a nematic matrix substance having a positive dielectric anisotropy, which component exhibits a pure red color in display.

SUMMARY OF THE INVENTION

In accordance with the invention, these and other objects are achieved herein by the provision of compounds for the guest host effect which are derivatives of tetrazine of the general formula

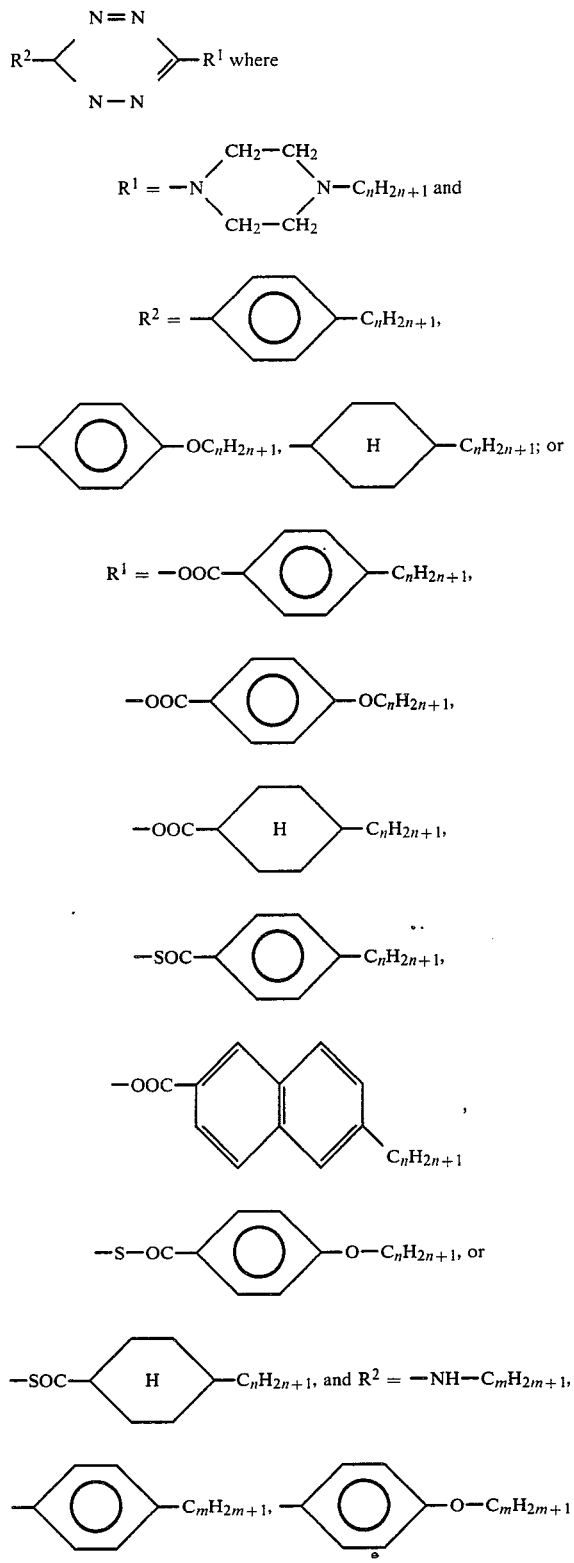

with m n=1 to 10.

The new derivatives of tetrazine have a negative dichroism with an absorption maximum of 510 to 530 nm, lending them and their mixtures a true red color hue. This position of the absorption maximum is very surprising, since the large number of previously produced tetrazine derivatives described in DD Patent Nos. 137 117; 137,118, 137,242, 151,950 always had the absorption maximum at 550 nm, independent of the substituents of the tetrazine rings. The new tetrazine derivatives have liquid crystalline characteristics themselves and also are very stable against light radiation.

The invention will be explained by means of the following embodiments.

EXAMPLE 1

Preparation of the Liquid Crystalline Ester of the 6-Alkylamino-1,2,4,5-Tetrazine-3-ols The synthesis follows the scheme below.
The synthesis occurs according to the general formula:

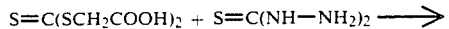

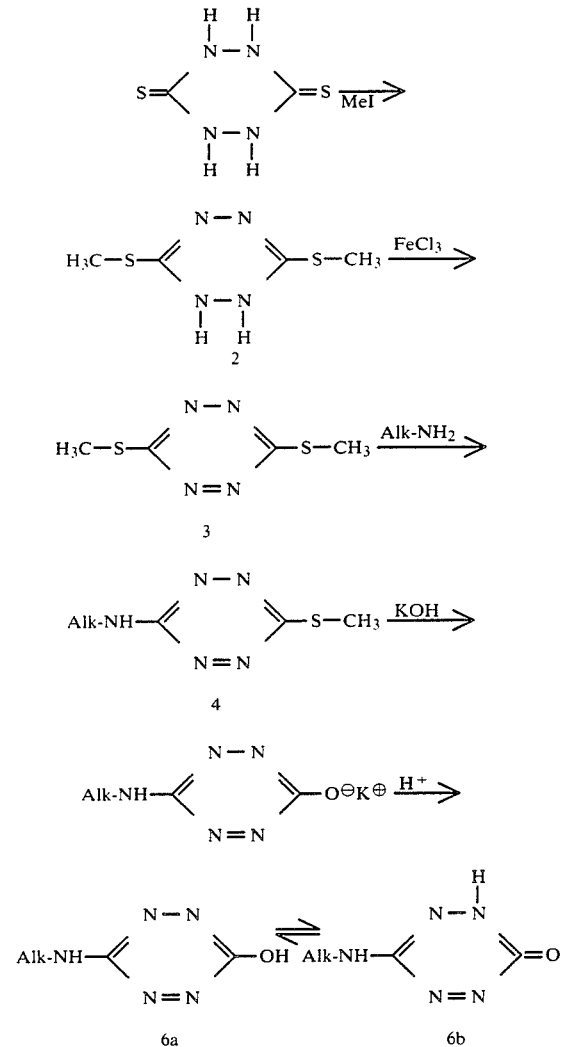

1. 6-n-Alkylamino-3-Methylthio-1,2,4,5-Tetrazine (4)

0.02 Mol 3.5 bis(methylthio)-1,2,4,5-tetrazine is heated at reflux with an equimolar amount of the n-alkylamine for three hours in 30 ml ethanol. The reaction solution then is reduced to dryness and crystalized from petroleum ether. For 6-n-hexyl-amino-3-methylthio-1,2,4,5-tetrazine, the yield was 68%, M.p. 54° C.

2. 6-n-Alkylamino-1,2,4,5-Tetrazine-3-ol (6)

0.2 Mol 6-n-alkylamino-3-methylthio-1,2,4,5-tetrazine (4) is dissolved in 100 ml ethanol and 0.4 mol pulverized KOH is added. The solution then is heated for three hours at reflux to complete the reaction, as determined by thin-film chromatography (Benzene/acid ester 3:1). The reaction solution is reduced to dryness and the crude potash salt of the 6-n-alkylamino 1,2,4,5-tetrazine-3-ols is absorbed in water, and the corresponding hydroxytetrazine settled by acidification with hydrochloric acid. The deposit then is vacuum dried, washed with water and dried. Recrystallization from benzene results in a red powder.

| Alkyl | °C. | Yield % |
|---|---|---|
| n-C$_6$H$_{13}$ | 133 | 58% |
| n-C$_8$H$_{17}$ | 128 | |
| n-C$_{10}$H$_{21}$ | 115–119 | |

(b) Synthesis of the ester of the 6-alkylamino-1,2,4,5-tetrazine-3-ols

The esterification of 6a with acid chlorides proceeds well in pyridine according to a variation of Einhorn as outlined in the following equation:

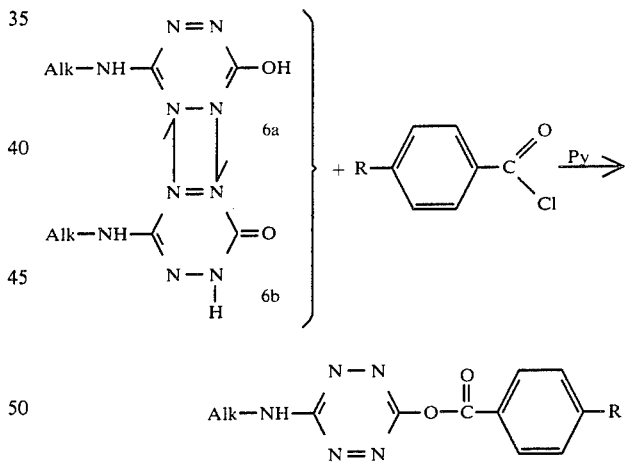

3. General procedure for the esterification of a 6-n-alkylamino-1,2,4,5-tetrazine-3-ol with 4-subst. benzoic acid chloride and with 4-n-alkyl-trans-cyclohexane-carboxylic-acid-chloride (7,8,9)

2 Mmol 6-n-alkylamino-1-2,4,5, tetrazine-2-ol is dissolved in 5 ml dry pyridine and mixed with 2 mmol of the acid chloride. After an hour, the reaction is complete, according to the thin film chromatogram (benzene/acetic ester 3:1). The product then is poured over icewater, acidified with HCL and the orange color ester absorbed in ether is. The ether solution is washed with water, dilute hydrochloric acid and saturated bicarbonate solution and again with water several times.

Following drying of the ether solution with Na$_2$SO$_4$, volume is reduced and the ester purified by several recrystallizations. The yields are between 60 and 70%. The melting and phase transformation temperatures of the new compounds are listed in Tables 1 to 3.

TABLE 1

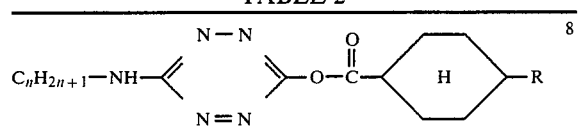

| No. | n | R | K | S | N | I |
|---|---|---|---|---|---|---|
| 7/1 | 6 | OC$_4$H$_9$ | . 83 | — | (. 73) | . |
| 7/2 | 6 | OC$_5$H$_{11}$ | . 63.5 | — | . 69.5 | . |
| 7/3 | 6 | OC$_6$H$_{13}$ | . 67.5 | — | . 73.5 | . |
| 7/4 | 6 | OC$_7$H$_{15}$ | . 73 | — | (. 73) | . |
| 7/5 | 6 | OC$_8$H$_{17}$ | . 81.5 | — | (. 74.5) | . |
| 7/6 | 6 | C$_6$H$_{13}$ | . 58 | — | — | . |
| 7/7 | 6 | C$_8$H$_{17}$ | . 58.5 | — | — | . |
| 7/8 | 6 | CN | . 110 | — | — | . |
| 7/9 | 8 | OC$_5$H$_{11}$ | . 65.5 | — | . 73 | . |
| 7/10 | 8 | C$_8$H$_{17}$ | . 64 | — | (. 53.5) | . |
| 7/11 | 8 | CN | . 103 | — | — | . |
| 7/12 | 10 | OC$_5$H$_{11}$ | . 71.5 | — | . 74 | . |
| 7/13 | 10 | C$_8$H$_{17}$ | . 72 | — | (. 63.5) | . |

TABLE 2

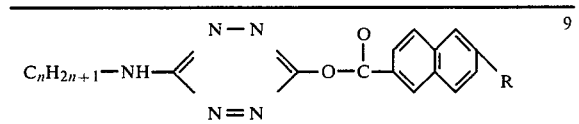

| No. | n | R | K | S | N | I |
|---|---|---|---|---|---|---|
| 8/1 | 6 | C$_2$H$_5$ | . 80 | — | — | . |
| 8/2 | 6 | C$_6$H$_{13}$ | . 82 | — | — | . |
| 8/3 | 6 | C$_7$H$_{15}$ | . 89.5 | — | — | . |
| 8/4 | 8 | C$_7$H$_{15}$ | . 84.5 | (.81) | — | . |

TABLE 3

| No. | n | R | K | N | I |
|---|---|---|---|---|---|
| 9/1 | 6 | C$_4$H$_9$ | . 98 | (. 93.5) | . |
| 9/2 | 6 | C$_8$H$_{17}$ | . 111.5 | — | . |

These esters are all orange and absorb between 510–530 mm.

EXAMPLE 2

Preparation of the liquid-crystalline ester of the 6-(4-n-alkylphenyl)-1,2,4,5-tetrazine-3-ol and 6-(4-n-alkylphenyl)-1,2,4,5-tetrazine-3-thiole The synthesis follows this scheme:

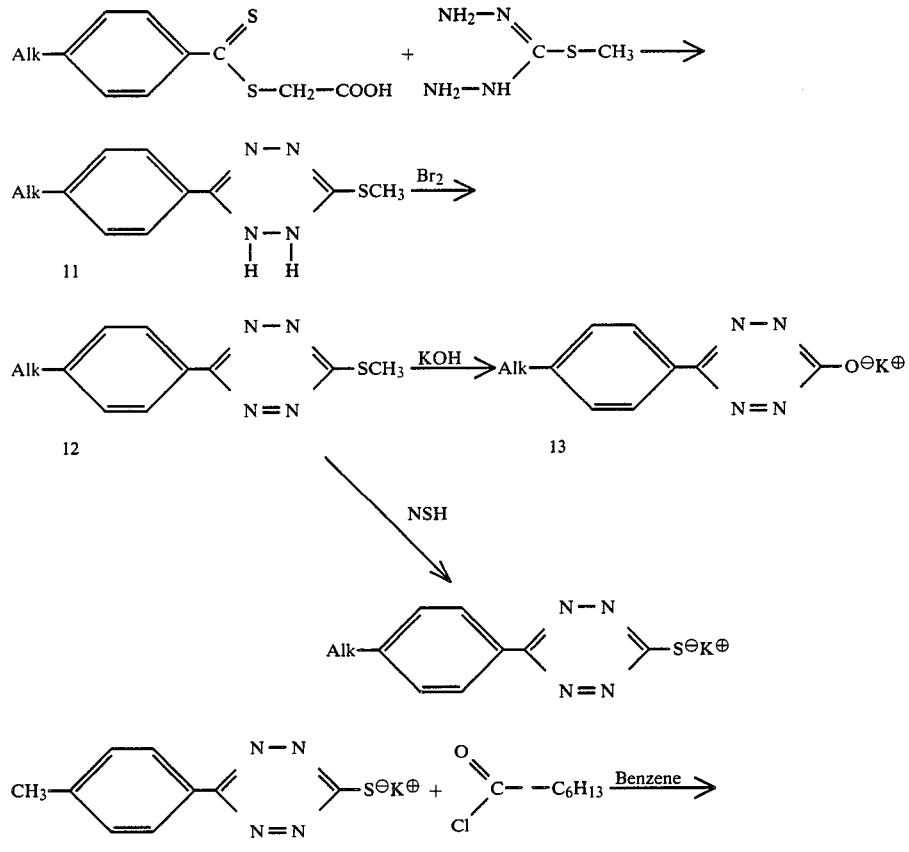

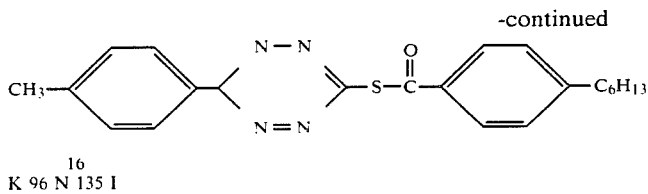

16
K 96 N 135 I

4. S-(4-n-Alkylphenyl)-thiocarbonyl thio acid chloride (10)

1 Mol carbon disulfide is added during cooling to a Grignard reagent prepared from 1 mol 4-n-alkyl bromobenzene, and the mixture is allowed to stand overnight. The reaction solution then then is hydrolyzed during ice cooling. Under vacuum the ether is distilled off until the aqueous phase is to approximately 2 l. Then 1 mol chloracetic acid, neutralized with sode, and dissolved in 500 ml water, is added to the aqueous phase. After 24 hours the aqueous solution is acidified with concentrated HCl. A dark red oil separates, which hardens into a semi-salt after approximately 3 hours. This semi-salt is absorbed in ether, the ether solution washed with water and saturated NaCl solution, dried with $Na_2SO_4$ and reduced. When the product is an oil, this oil is treated with petroleum ether until it crystallizes. Recrystallization is carried out from benzene (80° to 110° C.).

TABLE 4

| No. | R | M.P. [°C.] | Yield: [%] |
|---|---|---|---|
| 10/1 | $CH_3$ | 119 | 20 |
| 10/2 | $n-C_3H_7$ | 107 | 16 |
| 10/3 | $n-C_6H_{13}$ | 101 | 13 |

5. (4-n-Alkoxyphenyl)-thioxomethyl-thio-acid chlorides (17)

Compounds 17 of general formula are produced according to the well-known method of Jensen and Pedersen (Acta Chem. Scand. 15, 1087 (1961)), using 4-n-alkoxybenzaldehyde as the starting material and going through the thiopiperidine. Representatives compounds in this series are characterized in Table 5.

TABLE 5

| R | F. [°C.] | Yield$^x$ [%] |
|---|---|---|
| $n-C_4H_9$ | 115 | 77,5 |
| $n-C_5H_{11}$ | 87,5 | 75 |

$^x$relative to the thiopiperidine 6. 6-(4-n-propylphenyl)-3-methylthio-1.2-dihydro-1,2,4,5-tetrazine (11)

0.117 Mol (16 ml) triethylamine in 30 ml pyridine is added dropwise a period of 15 minutes into 0.117 mol (29 g) of the hydroiodide of hydrazinecarbohydrazonothio-acid methyl-ester in 350 ml pyridine, while while cooling with ice. While maintaining ice cooling, a solution of 0.1 mol (25.4 g) [[(4-n-propylphenyl)-thiooxymethyl]thio]-acid chloride, 0.1 mol (6.8 g) imidazole and 0.1 mol (14.5 ml) triethylamine in 300 ml pyridine are added to the yellow solution over a period of 1.5 hours. The solution is stirred for another two hours and subsequently poured over a volume of three times as much of ice water. The yellow dyestuff is vacuum dried, washed with water and dried. The yellow dyestuff product turns red in contact with air. Other 1.2-dihydro-tetrazines, listed in Table 6, were synthesized in an analogous manner.

| R | M.P. °C.$^{(x)}$ | Yield % |
|---|---|---|
| $CH_3$ | 201–206 | 37,5 |
| $n-C_3H_7$ | 180–85 | 20 |
| $n-C_6H_{13}$ | 145–50 | 26 |
| $n-C_5H_{11}-O-$ | raw material | |

$^{(x)}$following a one-time re-crystallization from ethanol 7. 6-(4-n-Propylphenyl)-3-methylthio-1,2,4,5-tetrazine (12)

0.0163 Mol (4.05 g) of 6-(4-n-propylphenyl)-3-methylthio-1.2-dihydro-1,2,4,5-tetrazine is dissolved in 80 ml crystalline acetic acid at 40° C. and 18 ml of a 1-molar $Br_2$-crystalline acetic acid solution is added dropwise. The solution is stirred for one hour and subsequently poured over ice water. The red dyestuff is vacuum dried, washed with water and dried. Recrystallization from ethanol provides 3.4 g of red crystals. M.pt.: 78°–79° C. The compounds characterized in Table 7 are made in an analogous fashion manner.

TABLE 7

| R | M.Pt. °C. | Yield % |
|---|---|---|
| $CH_3$ | 124–25 | 70 |
| $n-C_3H_7$ | 78–79 | 85 |
| $n-C_6H_{13}$ | 65 | 78,5 |
| $n-C_5H_{11}-O-$ | 89–91 | 75 |

8. 4-Subst. benzoic acid-[6-(4-n-alkylphenyl)-1,3,4,5-tetrazinyl-(3)-ester](15)

0.00172 Mol 6-(4-n-alkylphenyl)-3-methylthio-1,2,4,5-tetrazine (12) and 95 mg (0.0017 mol) KOH are heated in 30 ml ethanol for three hours at reflux (thin-film chromatogram shows complete transformation). Subsequently, the alcohol is reduced to dryness and the crude potash salt of the 6-(4-n-alkyl-phenyl)-1,2,4,5-tetrazine-3-ol is suspended in 20 ml of absolute benzene. Then 0.0017 mol of the corresponding acid chloride is added and the mixture is heated for 3 hours at reflux.

Following cooling, the insoluble product is filtered off, the benzene solution washed three times with saturated bicarbonate solution, once with water, dried with Na$_2$SO$_4$ and reduced in volume. Th red deystuff product is recrystallized several times from a solvent, e.g. the alkyl subst. benzoic acid ester from petroleum ether and in the case of the 4-cyanobenzoic acid ester from methanol. The yields are approximately 50%.

The compounds are listed in Table 8.

TABLE 8

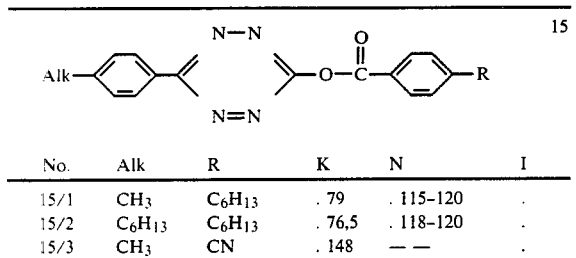

| No. | Alk | R | K | N | I |
|---|---|---|---|---|---|
| 15/1 | CH$_3$ | C$_6$H$_{13}$ | . 79 | . 115–120 | . |
| 15/2 | C$_6$H$_{13}$ | C$_6$H$_{13}$ | . 76,5 | . 118–120 | . |
| 15/3 | CH$_3$ | CN | . 148 | — — | . |

9. 4-Hexylthiobenzoic acid-S-[6-(4-methylphenyl)-1,2,4,5-tetrazinyl-(3)-ester] (16)

Compound of series 16 was synthesized according to the method described under 8 above for the production of 4-subst. benzoic acid-[6-(4-n-alkylphenyl)-1,2,4,5-tetrazinyl-(3)-esters] (15) using anhydrous potassium hydrosulfide in place of KOH. Recrystallization was carried out from methanol and petroleum ether. K 96 N 135 I

EXAMPLE 3

Preparation of the 6-(4-n-alkyl of alkoxyphenyl)-3-(4-N-alkylpiperazinyl-1-)-1,2,4,5-tetrazines

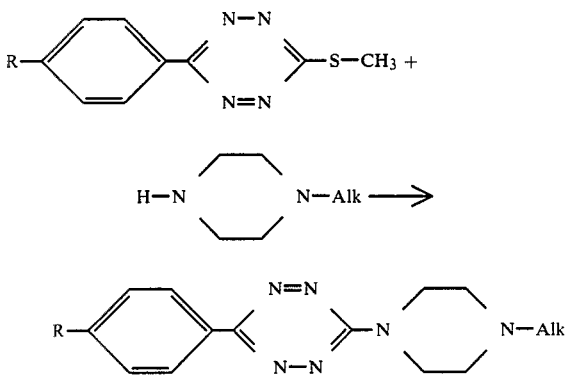

10. 6-(4-n-Alkyl of alkoxyphenyl)-3-(4-N-alkylpiperazinyl-1-1,2,4,5-tetrazine (18)

500 mg and the 6-(4-n-alkyl or alkoxyphenyl)-3-methylthio-1,2,4,5-tetrazines is mixed with a three-fold excess of 4-N-alkylpiperazine in 30 ml ethanol and the mixture is heated at reflux for three hours. The course of the reaction is followed by thin film chromatography using benzine/acetic ester.

The ethanol solution then is reduced to dryness and the residue is recrystallized from methanol to a constant clearing point. The yields are around 70% of theoretical. The compounds are listed in Table 9.

TABLE 9

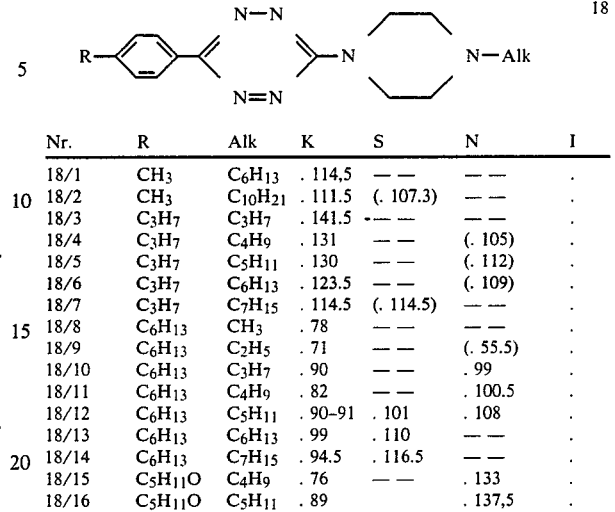

| Nr. | R | Alk | K | S | N | I |
|---|---|---|---|---|---|---|
| 18/1 | CH$_3$ | C$_6$H$_{13}$ | . 114,5 | — — | — — | . |
| 18/2 | CH$_3$ | C$_{10}$H$_{21}$ | . 111.5 | (. 107.3) | — — | . |
| 18/3 | C$_3$H$_7$ | C$_3$H$_7$ | . 141.5 | • — — | — — | . |
| 18/4 | C$_3$H$_7$ | C$_4$H$_9$ | . 131 | — — | (. 105) | . |
| 18/5 | C$_3$H$_7$ | C$_5$H$_{11}$ | . 130 | — — | (. 112) | . |
| 18/6 | C$_3$H$_7$ | C$_6$H$_{13}$ | . 123.5 | — — | (. 109) | . |
| 18/7 | C$_3$H$_7$ | C$_7$H$_{15}$ | . 114.5 | (. 114.5) | — — | . |
| 18/8 | C$_6$H$_{13}$ | CH$_3$ | . 78 | — — | — — | . |
| 18/9 | C$_6$H$_{13}$ | C$_2$H$_5$ | . 71 | — — | (. 55.5) | . |
| 18/10 | C$_6$H$_{13}$ | C$_3$H$_7$ | . 90 | — — | . 99 | . |
| 18/11 | C$_6$H$_{13}$ | C$_4$H$_9$ | . 82 | — — | . 100.5 | . |
| 18/12 | C$_6$H$_{13}$ | C$_5$H$_{11}$ | . 90–91 | . 101 | . 108 | . |
| 18/13 | C$_6$H$_{13}$ | C$_6$H$_{13}$ | . 99 | . 110 | — — | . |
| 18/14 | C$_6$H$_{13}$ | C$_7$H$_{15}$ | . 94.5 | . 116.5 | — — | . |
| 18/15 | C$_5$H$_{11}$O | C$_4$H$_9$ | . 76 | — — | . 133 | . |
| 18/16 | C$_5$H$_{11}$O | C$_5$H$_{11}$ | . 89 | — — | . 137,5 | . |

The following examples illustrate the use of the new tetrazine derivatives of the invention.

EXAMPLE I

The new compound 7/2 4-n-pentyloxybenzoic acid-[6-n-hexyl-amino-1,2,4,5-tetrazinyl-(3)-ester]

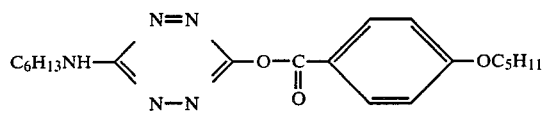

has two absorption bands at γ max=518 nm or 391 nm and has a brilliant red color in its liquid-crystalline stage state.

The following mixture using 7/2 was prepared as follows:

| | mol-% |
|---|---|
| Mi 383 | 7.7 |
| Compound 7/2 | |

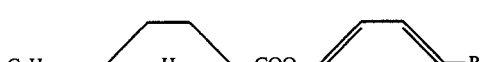

| n | R | |
|---|---|---|
| 4 | —OC$_2$H$_5$ | 12.2 |
| 4 | —OC$_6$H$_{13}$ | 20.0 |
| 3 | —CN | 20.7 |
| 4 | —CN | 18.7 |
| 5 | —CN | 20.7 |

The mixture has the following properties:

K—3N61I

At 25° C. measured with light γ=510 nm Degree of order S=0.78, dichroite relationship 6.3

In an electro-optical cell with a planar orientation of the nematic liquid crystal on both electrode surfaces and a layer thickness of d=11 μm, the threshold voltage is U$_o$=2.2 V at 18° C.

EXAMPLE II

The mixture Mi 440 has the following composition:

| | mol-% |
|---|---|
| Compound 7/2 | 8.4 |

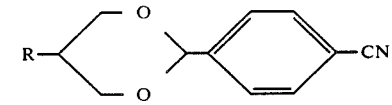

| R | |
|---|---|
| $C_3H_7-$ | 46.6 |
| $C_6N_{13}-$ | 40.4 |
| | 4.6 |

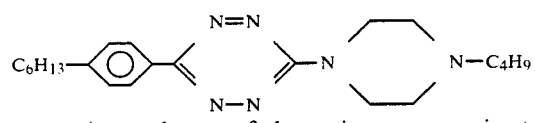

Mi 440 has the following properties:
Clearing point 30° C.
Degree of order S=0.33 at 20° C., dichroite relationship 1.7 ($\gamma=510$ nm)

EXAMPLE III

Compound No. 18/13

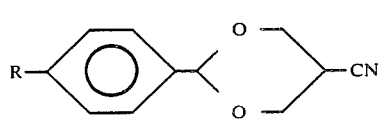

has a maximum degree of absorption at approximately 530 nm.

The mixture Mi 436 has the following composition:

| | | mol-% |
|---|---|---|
| Compound 18/13 | | 7.2 |

| n | R | |
|---|---|---|
| 4 | $-OC_2H_5$ | 12.4 |
| 4 | $-OC_6H_{13}$ | 20.1 |
| 3 | $-CN$ | 20.8 |
| 4 | $-CN$ | 18.7 |
| 5 | $-CN$ | 20.8 |

The mixture does not crystallize at −12° C., even after a year; clearing point 73° C.

EXAMPLE IV

The mixture Mi 441 has the following composition:

| | mol-% |
|---|---|
| Compound 18/11 | 8.2 |

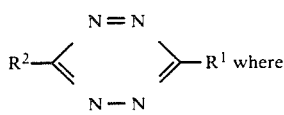

| R | |
|---|---|
| $C_3H_7-$ | 46.7 |
| $C_6H_{19}-$ | 40.5 |
| | 4.6 |

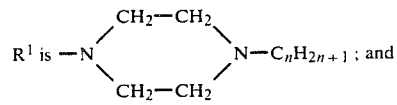

Clearing point 44° C.
Degree of order S=0.375 at 20° C.
Dichroitic relationship 1.9 ($\gamma=552$ nm).

We claim:
1. Liquid crystal compounds for the guest-host effect which are derivatives of tetrazine of the general formula:

where $R^1$ is

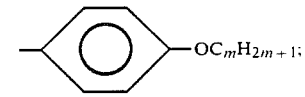

$-N\begin{pmatrix}CH_2-CH_2\\CH_2-CH_2\end{pmatrix}N-C_nH_{2n+1}$ ; and $R^2$ is

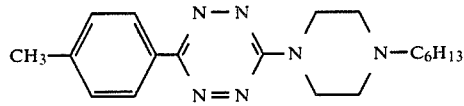 $-C_mH_{2m+1}$ or

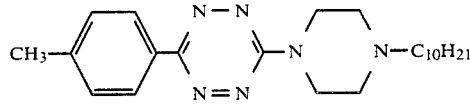 $-OC_mH_{2m+1}$;

and m and n are 1 to 10.

2. A liquid-crystal substance, according to claim 1, which is

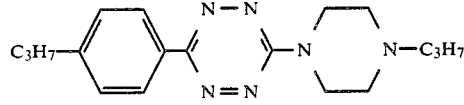

3. A liquid-crystal substance, according to claim 1, which is

[structure with CH3, N=N, N-N, piperazine, N-C10H21]

4. A liquid-crystal substance, according to claim 1, which is

[structure with C3H7, N=N, N-N, piperazine, N-C3H7]

5. A liquid-crystal substance, according to claim 1, which is

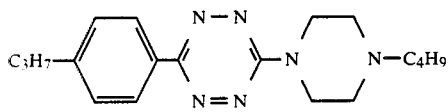

6. A liquid-crystal substance, according to claim 1, which is

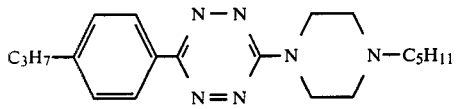

7. A liquid-crystal substance, according to claim 1, which is

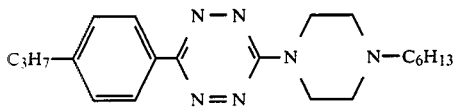

8. A liquid-crystal substance, according to claim 1, which is

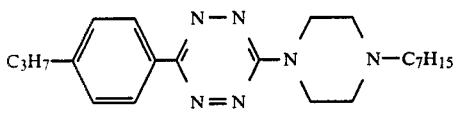

9. A liquid-crystal substance, according to claim 1, which is

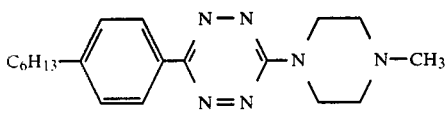

10. A liquid-crystal substance, according to claim 1, which is

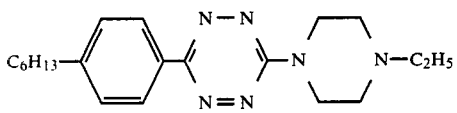

11. A liquid crystal substance, according to claim 1, which is

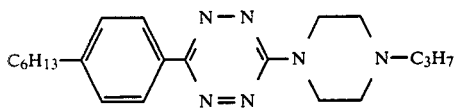

12. A liquid-crystal substance, according to claim 1, which is

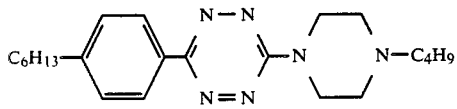

13. A liquid-crystal substance, according to claim 1, which is

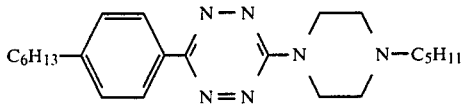

14. A liquid-crystal substance, according to claim 1, which is

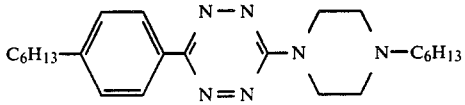

15. A liquid-crystal substance, according to claim 1, which is

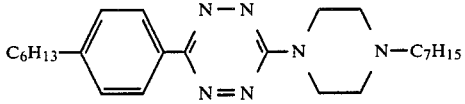

16. A liquid-crystal substance, according to claim 1, which is

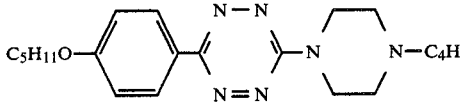

17. A liquid-crystal substance, according to claim 1, which is

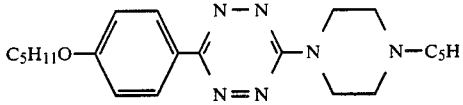

18. Liquid crystal mixtures for the guest-host effect which contain about 1 to 15 mol % of at least one derivative of tetrazine according to any one of claims 1 and 2 to 17.

19. In a positive contrast opto-electronic display component comprising a dye having a negative dichroism and a nematic matrix substance having a positive dielectric anisotropy, the improvement in which the dye is a compound according to any one of claims 1 and 2 to 17.

20. In a positive contrast opto-electronic display component according to claim 19, the improvement wherein said dye is present in an amount of about 1 to 15 mol %.

21. A liquid crystal mixture for the guest-host effect according to claim 18, containing 7.2 mol % of

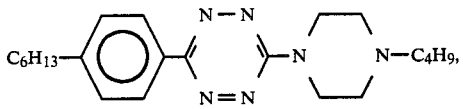

12.4 mol - % of C₄H₉—⟨H⟩—COO—⟨◯⟩—OC₂H₅,

-continued
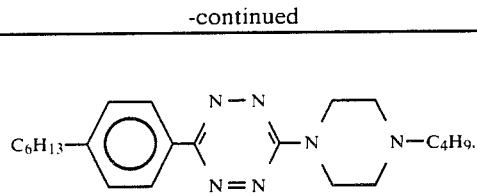
20.1 mol - % of 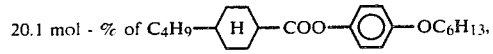
-continued
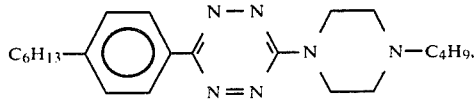
20.8 mol - % of 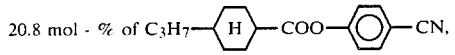,
18.7 mol - % of C$_4$H$_9$—⟨H⟩—COO—⟨○⟩—CN, and
20.8 mol - % of 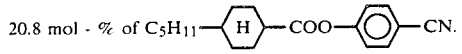.
* * * * *